United States Patent [19]

MacConnell

[11] Patent Number: 4,787,963

[45] Date of Patent: Nov. 29, 1988

[54] METHOD AND MEANS FOR ANNEALING COMPLEMENTARY NUCLEIC ACID MOLECULES AT AN ACCELERATED RATE

[75] Inventor: William P. MacConnell, Cardiff, Calif.

[73] Assignee: Syntro Corporation, San Diego, Calif.

[21] Appl. No.: 46,652

[22] Filed: May 4, 1987

[51] Int. Cl.[4] ............................................. C12N 15/00
[52] U.S. Cl. .............................. 204/180.1; 204/299 R; 204/301; 435/289; 435/287; 435/6; 935/78
[58] Field of Search ............... 435/291, 287, 678, 803, 435/289; 204/180.1, 299 R, 180.2, 301

[56] References Cited

PUBLICATIONS

Maniatis, T. et al., "Molecular Cloning: A Laboratory Manuel" Cold Spring Harbor Laboratory (1982) pp. 191–198.

Grunstein, M. et al., "Colony Hybridization: A Method for the Isolation of Cloned DNAs that Contain a Specific Gene", Proc. Nat. Acad. Sci. USA vol. 72, No. 10, pp. 3961–3965 (1975).

Meinkoth, J. "Hybridization of Nucleic Acids Immobilized on Solid Supports" Analytical Biochemistry 138, pp. 267–284 (1984).

Thomas, P. "Hybridization of Denatured RNA and Small DNH Fragments Transferred to Nitrocellulose", Proc. Natl. Acad. Sci. USA vol. 77, No. 9, pp. 5201–5205 (1980).

Mulcahy L., "DNA Probes: An Overview" ACPR, Nov. 1986, pp. 14–19.

Wetmur, V. "Acceleration of DNA Renaturation Rates" Biopolymers, vol. 14, pp. 2517–2524 (1975).

Chang, C. T. et al., "Effects of Microscopic and Macroscopic Viscosity on the Rate of Renaturation of DNA" Biopolymers, vol. 13, pp. 1847–1858 (1974).

Kohne, D. "Application of DNA Probe Tests to the Diagnosis of Infectious Disease" ACPR, Nov. 1986, pp. 20–29.

*Primary Examiner*—John F. Niebling
*Assistant Examiner*—John S. Starsiak
*Attorney, Agent, or Firm*—Joseph C. Schwalbach

[57] ABSTRACT

Method and means for accelerating the rate of hybridization of nucleic acid probes with complemental target sequences in probe assays of the filter binding or sandwich filter binding formats. The nucleic acid probes are electrophoretically concentrated at membrane means including at least a dialysis type membrane and to which the target sequences are bound. The rate of hybridization can be further enhanced by means for moving concentrated unannealed probe molecules successively in various directions along the surface of the membrane means to which the target sequences are bound. The invention further includes method and means for electrophoretically removing from the membrane means unannealed probe molecules which became adsorbed to the membrane means during hybridization. In one embodiment of the invention the membrane means comprises a cellulose dialysis membrane in laminate relation with a nitrocellulose or nylon filter having target sequence molecules bound to the surface thereof facing the dialysis membrane. In another embodiment of the invention the membrane means comprises a dialysis membrane to one side of which the target sequence molecules are bound.

38 Claims, 2 Drawing Sheets

METHOD AND MEANS FOR ANNEALING COMPLEMENTARY NUCLEIC ACID MOLECULES AT AN ACCELERATED RATE

BACKGROUND OF THE INVENTION

Technical Field

This invention relates to nucleic acid hybridization, and more particularly to a method and means for annealing complementary nucleic acid molecules at an accelerated rate.

The use of nucleic acid probes to detect particular target nucleic acid sequences in samples containing one or more nucleic acids is of vast utility to research, medicine, and forensics. Because nucleic acid probes are highly specific for their target sequences, they can be used as diagnostic reagents to detect the presence of a particular nucleic acid, as well as features within that nucleic acid. Commercial nucleic acid probe assays are being developed for the detection of infectious microorganisms, viruses, mutations in the human genome, as well as for fingerprinting human and other species' genomes. Research applications of nucleic acid probes are manifold, having been extensively utilized in recombinant DNA work for over 10 year.

All nucleic acid probe assays require a step in which a labeled or tagged probe nucleic acid is hybridized to a target sequence by annealing of the probe and target nucleic acids. The time required for such hybridization is often a critically limiting factor in nucleic acid probe assays which are performed in a nonresearch or medical setting in which minimization of the time required for performance of the assay is of importance. The rate of the annealing reaction is affected by several factors, such as ionic strength, temperature, concentration of the reactant molecules, and the presence of denaturing solvent. Concentration of the reactant molecules is perhaps the most important of these factors, because it limits the rate at which the random collisions between the complementary single-stranded nucleic acid probe and target sequences occur as required to bring about annealing thereof to each other in a hybridization reaction. Once two complementary nucleic acid molecules have appropriately collided, they rapidly anneal to form a thermodynamically stable duplex that does not spontaneously dissociate into its single-stranded components.

In the simplest of forms, nucleic acid probe hybridization involves the detection of a target nucleic acid (RNA or DNA), either bound to a solid support or free in solution, using a labelled complementary probe nucleic acid. Nucleic acid probe assays fall into two general categories, i.e., free-solution probe assays and filter (or solid support) binding assays.

In the free-solution probe assays the target and probe nuceic acids are freely dissolved in solution. Target nucleic acid (RNA or DNA) is first extracted from the sample, denatured to convert it to single-stranded form, and dissolved in hybridization buffer. Extraction of target nucleic acid from the sample and denaturation thereof can be accomplished by the procedure disclosed by T. Maniatis et al in "Molecular Cloning: A Laboratory Manual", Cold Spring Harbor Laboratory (1982), pages 191 to 198. A labelled probe DNA or RNA complementary to the target nucleic acid is added to this solution and allowed to hybridize to the target sequence. When the hybridization reaction is complete, a suspension of hydroxyapatite (calcium hydroxide) is added. The hydroxyapatite selectively binds double-stranded probe/target nucleic acid duplexes as well as other double-stranded molecules, but does not bind unannealed single-stranded molecules. The insoluble hydroxyapatite with probe/target sequence duplex bound thereto is separated from the hybridization medium by centrifugation and washed to remove traces of unreacted probe molecules. If the probe has an isotopic label, the amount of probe bound to the hydroxyapatite is quantitated by scintillation counting. Other conventional means can be used to detect and quantitate nonisotopically labeled probe bound to the hydroxyapatite.

Filter binding DNA probe assays can be performed in several different ways. One way involves binding of single-stranded sample nucleic acid (RNA or DNA) to a nitrocellulose or nylon filter in an irreversible manner. This can be accomplished by applying the nucelic acid to the filter, and then baking it at a temperature of 70 C. for from about one to about two hours under reduced pressure, i.e. at a pressure of less than 1 psi. The filter with sample nucleic acid bound thereto, is then prehybridized by placement thereof in an aqueous solution containing salts, protein, nonreactive DNA or RNA, sodium dodecyl sulfate detergent, buffer, EDTA, and formamide to block nonspecific binding sites on its surface. This procedure is disclosed by Grunstein M. et al, in their paper entitled "Colony Hybridization: A Method for the Isolation of Cloned DNAs that Contain a Specific Gene", *Proc. Nat'l Acad. Sci.* 72(10): 3961–3965, 1975.

When the prehybridization step is complete, labeled probe DNA or RNA, dissolved in an aqueous solvent, is added to the solution containing the prehybridized filter to which the sample nucleic acid is bound. The probe is allowed to hybridize with the filter-bound sample nucleic acid until formation of sample/probe duplexes has gone to completion. The filter is then removed from the hybridizaton solution and washed with a buffered salt solution at a controlled temperature to remove nonspecifically bound labeled probe sequences. After the washing step, only labeled probe molecules which are specifically annealed to matching sample target sequences remain on the filter. The washed filter can be autoradiographed, or other appropriate conventional means can be used to detect the label and determine the amount and location of the bound probe, and thereby the location of the complementary sample sequences originally applied.

The foregoing procedures employ techniques disclosed in the following prior art literature references:

Meinkoth, J and Wahl, J., "Hybridization of Nuleic Acids Immobilized on Solid Supports", *Analytical Biochemistry*, 138: 267, 1984; and Thomas, P. S., "Hybridization of Denatured RNA and Small DNA Fragments Transferred to Nitrocellulose", *Proc. Nat'l Acad. Sci.*, 77 (9): 5201–5205, 1980.

A variation of the filter-binding procedure is the sandwich filter-binding assay. This procedure is similar to the filter binding assay, except that it involves two nucleic acid probes. The first probe is unlabeled, and before the assay procedure is undertaken, this probe is covalently bound to the nitrocellulose or nylon filter. The thus prederivitized filter, with the first probe bound thereto, is prehybridized in the same kind of buffer solution as was described above, after which a solution containing single-stranded nucleic acid target sequences extracted from the sample as aforedescribed, are added to the prehybridizaton solution containing the filter. Sample nucleic acid target sequences which are complementary to the bound first probe sequences become adherent to the filter by annealing to said first probe sequences.

A second labeled DNA or RNA probe which is complementary to the filter-bound sample target sequences, but is nonoverlapping with the first filter-bound probe, is then annealed to the sample target sequences and thereby also becomes bound to the filter. Each resultant bound sandwich nucleic acid complex contains the first probe bound to the filter, the target sample nucleic acid sequence annealed to the first probe, and the second labeled probe annealed to the overhanging ends of the target nucleic acid sequence. The steps of a sandwich filter binding assay can be carried out sequentially as aforedescribed, or the sample target sequence and labeled secondary probe nucleic acids can be added to the hybridization medium at the same time. This procedure is discussed by Mulcahy, L., in "DNA Probes: An Overview", *ACPR:* 14–19, November 1986.

It has been found that the rate of DNA or RNA hybridizaton in the free-solution type probe assay can be accelerated by the addition to the hybridization medium of water soluble polymers, such as dextran sulfate, polyvinyl pyrrolidone, or tetraethyl ammonium chloride. The mechanism by which these polymers enhance the rate of hybridization of DNA or RNA molecules is believed to involve a reduction in the effective solvent volume available to the nucleic acids in solution. The negatively charged polymers complex with available solvent molecules from around the nucleic acid molecules, resulting in an effective increase in concentration of DNA or RNA molecules relative to each other. Such concentration is believed to be effective to increase the number of collisions between complementary sequences, and to thereby produce faster annealing rates.

Such rate enhancer compounds have been found to increase nucleic acid probe hybridization rates by 10 to 200 fold in free-solution probe assays, thereby making possible hybridization times of 1 to 2 hours, rather than overnight. In the case of short synthetic nucleic acid probes, hybridization reactions can be completed in less than 15 minutes if high concentrations of oligomeric probe, for example 1 milligram per milliliter, are used along with rate enhancer compounds. In general, however, the hybridization reaction for nucleic acid probe assays requires 1 to 2 hours when probes of 100 or more nucleotides in length are used in free-solution type hybridization assays. In contrast to results produced by these rate enhancer compounds in free-solution type assays, their use in filter binding type assays has been found to produce no significant rate enhancement.

References discussing the use of rate enhancer compounds are:
Wetnur, J., *Biopolymers,* 14: 2517–2524, 1975;
Chang, C. T. et al, *Biopolymers,* 13: 1847–1858, 1975; and
Kohne, D. E., *ACPR:* 20–29, November 1986.

In order to supply the frequent need of researchers and others to collect a dense amount of nucleic acid molecules, for example on a carrier membrane, instruments are available commercially which can separate nucleic acid from a gel or can isolate or concentrate nucleic acid molecules from a solution thereof. The operation of such electroelution or electrophoretic concentration devices takes advantage of the fact that, due to the presence of phosphate groups on the nucleic acid backbone, DNA and RNA in aqueous solution are highly negatively charged molecules. When a voltage is applied across platinum wire electrodes placed in a solution of RNA or DNA, the resulting current flow through the solution causes the negatively charged nucleic acid molecules to migrate toward the positive electrode (anode) and concentrate on its surface.

In the aforementioned commercial devices, this principle is used to electrophoretically concentrate the migrating DNA or RNA molecules from a solution, or from agarose or acrylamide containing such molecules, onto the surface of a liquid permeable, for example a cellulose, collector membrane which is impermeable to the nucleic acid molecules and is positioned to prevent such molecules from contacting the anode. Usually, devices of this sort are configured with two chambers separated by the membrane. In one chamber the gel or nucleic acid-containing moiety is placed in a buffered solution near but not against one side of the membrane. The second chamber contains only buffered solution in contact with the other side of the membrane so that aqueous solution contacts both sides of the latter. Platinum wire electrodes present in the respective chambers are connected to a constant direct voltage power supply, the electrode in the chamber containing the nucleic acid to be concentrated being connected to the negative terminal of the source to provide a cathode, and the other electrode being connected to the positive terminal thereof to provide an anode. The electric potential impressed across the electrodes by the source, causes current flow therebetween through the aqueous solutions and is effective to cause the negatively charged nucleic acid molecules in the cathode chamber electrophoretically to migrate toward and be concentrated onto the side of the membrane or disc exposed in the cathode chamber. The nucleic acid becomes deposited on the membrane or disc during the procedure. Upon completion of the concentration step, the electrodes are disconnected from the source, and the nucleic acid deposited on the membrane can be easily removed therefrom, as by washing.

Depending upon the type of membrane used therein, the commercial devices can also be used to bind to the membrane the nucleic acids concentrated thereon. For example, when a membrane of modified nylon is used, the nucleic acids concentrated thereon are bound thereto upon contact. On the other hand, when a membrane of nitrocellulose is used, the nucleic acids concentrated thereon can be bound thereto upon removal of the membrane from the instrument. Such binding can be accomplished by baking at a temperature of 70° C. for about one to about two hours at reduced pressure, i.e. less than 1 psi.

Examples of commercial electrophoretic concentration/elution instruments of the type discussed above are the Electro-Eluter/Concentrator available from C. B. S. Scientific, Del Mar, CA 92014; the preparative gel electrophoresis system (prep gel TM) available from Bethesda Research Laboratories, Bethesda, Md.; and the Trans-Blot Cell availabe from Bio-Rad, Richmond, CA.

SUMMARY OF THE INVENTION

The invention comprises an improved method and means for accelerating the rate of hybridization of a nucleic acid probe assay of the filter-binding or sandwich filter-binding type by electrophoretically concentrating nucleic acid probe molecules at membrane means to which target nucleic acid sequences are bound. Such electrophoretic concentration substantially increases the incidence of collisions of the probe sequences with the bound target sequences.

The invention further includes an improved method and means for electrophoretically moving unannealed probe sequences successively in various directions along the surface of the membrane means and in contact with the target sequences bound thereto. Such probe movement still further increases the incidence of collisions between the moving unannealed probe sequences and the bound target sequences.

The invention also includes an improved method and means for rapidly removing from the membrane means, prior to removal thereof from contact with the hybridization solution, unannealed probe sequences which became adsorbed to the membrane means during the hybridization step.

The improved method and means of the invention aforedescribed are well adapted for automated procedures, involve instrumentation which is simple and inexpensive in construction, and do not require skilled operating personnel.

BRIEF DESCRIPTION OF THE DRAWINGS

In the drawings, which illustrate one embodiment of the preferred form of improved instrument with which the method of the present invention can be practiced.

DESCRIPTION OF THE PREFERRED EMBODIMENT

Figures 1, 2:
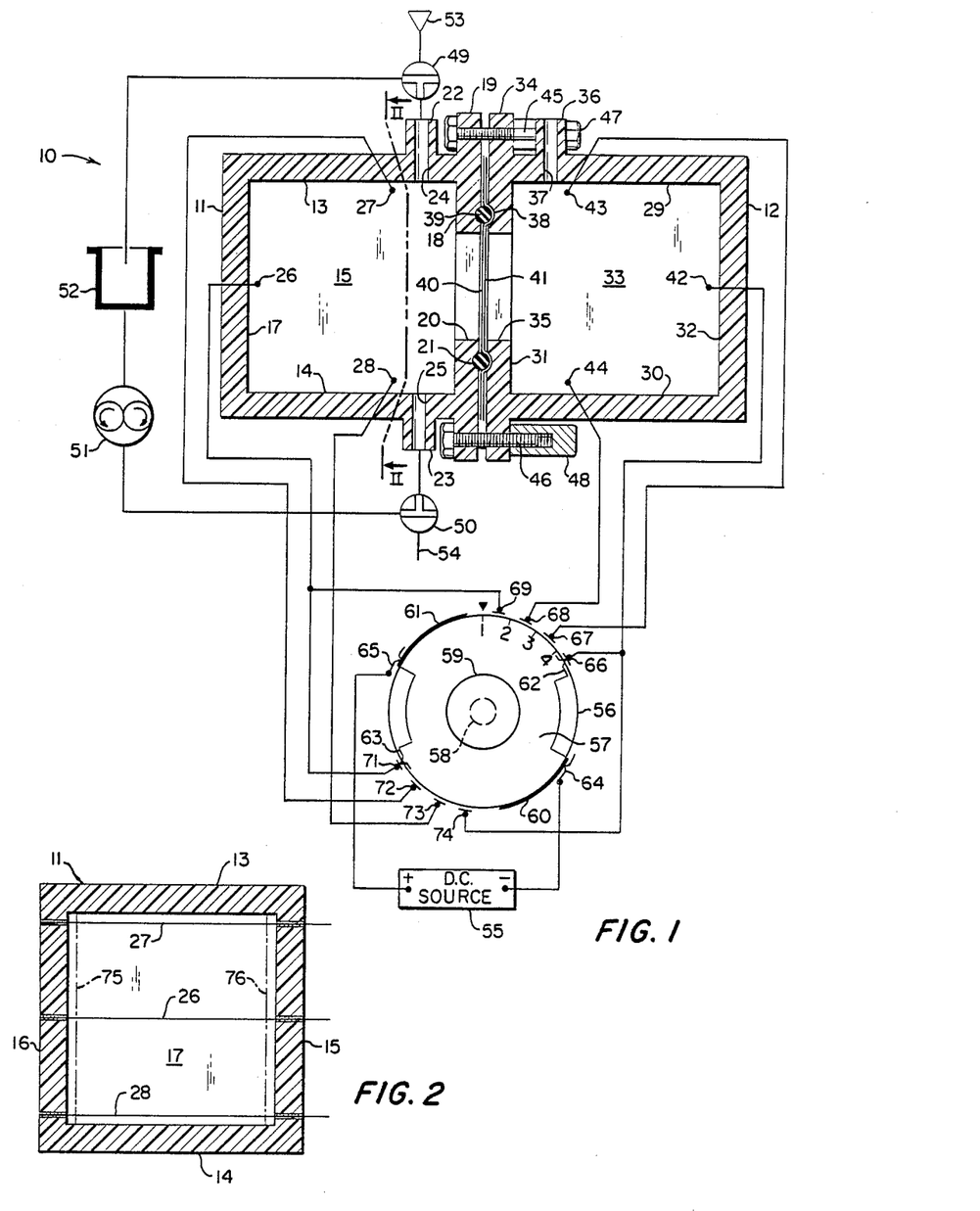
FIG. 1 is a semidiagrammatic illustration of the instrument showing the dual chambered receptacle in longitudinal section.
FIG. 2 is a transverse section taken along the line II—II of FIG. 1.

Referring to the FIG. 1 of the drawings, the instrument 10 comprises receptacle means which, in the illustrated embodiment, is formed by a pair of complementary similar chamber members 11 and 12 which may be cubical in shape and may be constructed of acrylic plastic or other suitable electrically insulating material. The chamber member 11 has parallel upper and lower horizontal side walls 13 and 14, parallel opposite vertical side walls 15 and 16, and parallel outer vertical and inner end walls 17 and 18. Inner end wall 18 projects outwardly beyond the side walls 13 to 16 of the chamber member 11 to provide a peripheral flange 19. The inner end wall 18 is formed with a generally centrally located aperture 20, which is preferably a circular bore and is spaced from the side walls 13 to 16. The surface of the inner wall 18 facing chamber member 12 is formed with a circular groove 21 which coaxially surrounds the aperture 20 in spaced relation and is semicircular in cross section.

The chamber member 11 is formed in the wall 13 with an external tubular projection 22 adjacent the flange 19, and is formed on the wall 14 with an external tubular projection 23 adjacent the flange 19. The projections 22 and 23 have bores 24 and 25, respectively, which open into the interior of chamber member 11, and are preferably coaxial and intersect the axis of the aperture 20 in wall 18.

As shown in FIG. 2, the walls 15 and 16 of the illustrated chamber member 11 are formed with coaxial bores through which electrode means in the form or a first central platinum wire electrode 26 sealingly projects, one end of said electrode projecting externally of the wall 15 as shown. As shown in FIG. 1, the electrode 26 preferably extends generally parallel with the walls 13, 14, 17 and 18, is disposed closely adjacent the wall 17, and preferably intersects the axis of the aperture 20 in wall 18.

The walls 15 and 16 are also formed with suitable coaxial bores in which electrode means in the form of an upper platinum wire electrode 27 is sealing mounted, one end of the electrode 27 extending externally of the wall 15 as shown in FIG. 2. As shown in FIG. 1, the electrode 27 is spaced laterally from the axis of the bore 20 and is preferably closely adjacent the wall 13, extends generally parallel with the walls 13, 14, 17 and 18, and is also adjacent the wall 18.

Walls 15 and 16 are further formed with coaxial bores in which is sealing received electrode means in the form of a lower platinum wire electrode 28, one end of which projects externally of the wall 15 as shown. The electrode 28 is spaced laterally from the axis of the bore 20, is disposed closely adjacent the wall 14 and, like electrode 27, is also adjacent the wall 18, said electrode preferably extending parallel with the walls 13, 14, 17 and 18 as shown.

The chamber member 12 has parallel upper and lower walls 29 and 30, parallel vertical inner and outer end walls 31 and 32, a vertical sidewall 33, and an opposite vertical sidewall parallel with wall 33 (not shown). The inner end wall 31 projects externally of the sidewalls of chamber 12, as shown, to provide a peripheral flange 34 corresponding to the flange 19. The wall 31 is also formed with a generally centrally located aperture 35 which is preferably a circular bore spaced from the side walls of chamber member 12. Aperture 35 preferably has the same diameter as the aperture 20 and is coaxial therewith. The wall 29 is formed with an external tubular projection 36 adjacent the wall 31 and having a bore 37 opening into the interior of the chamber member 12. The wall 31 is formed on the surface thereof facing the chamber member 11 with a circular groove 38 coaxial and in spaced relation with the aperture 35. Groove 38 has the same diameter as groove 21 and is in registration therewith. The groove 38 has a semicircular cross section like that of the groove 21.

A resilient O-ring 39 made, for example, of silicone rubber, is disposed in the circular grooves 21 and 38 as shown. Extending across the apertures 20 and 35 and O-ring 39, and clamped between the walls 18 and 31, is membrane means 40 which comprises at least a first membrane of the dialysis membrane type, preferably made of cellulose. Two such membranes which are satisfactory for use as a component of the membrane means 40 are available from Thomas Scientific, P.O. Box 779, Philadelphia, PA 19105, under the catalog numbers 3787-D10 and 3878-H45, both marketed under the trademark Spectra/Por ®. The 3787-D10 membrane has an exclusion molecular weight of 12,000 daltons and excludes nucleic acid sequences longer than about 37 nucleotides in length. The 3787-H45 membrane has an exclusion molecular weight of 3,000 and excludes nucleic acid sequences longer than about 9 nucleotide units in length.

In the illustrated form of the invention the membrane means 40 also includes a nitrocellulose or nylon membrane 41 of the filter type which is permeable to both liquid and to nucleic acid molecules. A suitable nitrocellulose membrane is the membrane available from Schleicher and Schuell, catalog No. BA85. The address of Schleicher and Schuell is 10 Optical Avenue, Keene, NH 03431. A suitable nylon membrane is the NEN Screen ® membrane available from New England Nuclear, 549 Albany Street, Boston, MA 02118. Membrane 41 is disposed in close laminate relation with the dialysis type membrane of the membrane means 40, and on the side thereof facing the chamber member 12.

The wall 33 of chamber member 12 and the wall opposite to it (not shown) are formed with suitable coaxial bores to sealing accomodate electrode means comprising the platinum wire electrode 42 which is spaced laterally from the axis of the bores 20 and 35, is disposed closely adjacent a second central wall 32, preferably intersects the axis of the bores 20 and 35, and is parallel with walls 29 to 32. The wall 33 and its opposing counterpart (not shown) are also formed with coaxial bores to sealing accomodate electrode means in the form of a platinum wire electrode 43 which is disposed closely adjacent the wall 29, is parallel with walls 29 to 32, and is also adjacent the wall 31 as shown. The wall 33 of chamber member 12 and its opposite counterpart are further formed with coaxial bores to sealing receive electrode means in the form of a lower platinum wire electrode 44 which is spaced laterally from the axis of the bores 20 and 35, is disposed closely adjacent the wall 30, is parallel with walls 29 to 32, and is also adjacent the wall 31 as shown. One end of the electrodes 42, 43 and 44 project externally of the chamber member 12 in the same manner that the electrodes 26 to 28 extend from chamber 11 as shown in FIG. 2. All of said electrodes may terminate in suitable external electrical terminal means (not shown) for easy connection thereof into an electrical circuit.

From the foregoing it will be apparent that central electrodes 26 and 42 comprises first and second electrodes which preferably intersect the axis of bores 20 and 35. It will also be apparent that the upper electrodes 27 and 43 comprise a first pair of third and fourth electrodes spaced laterally in the same direction from, e.g. above in FIG. 1, the axis of bores 20 and 35. It will be further apparent that the lower electrodes 28 and 44 comprise a second pair of third and fourth electrodes spaced laterally, e.g. below in FIG. 1, the axis of bores 20 and 35, and that said second pair of third and fourth electrodes is thus spaced on the opposite side of the axis of bores 20 and 35 from said first pair of third and fourth electodes.

The peripheral flanges 19 and 34 of chamber members 11 and 12 respectively are formed with coaxial bores to receive at least three equally spaced bolts, only two of which, 45 and 46 are shown. Threaded on the bolts 45 and 46 and the corresponding additional bolt(s) (not shown), are externally faceted or knurled nuts 47 and 48 as shown. The bolts 45 and 45 and cooperating nuts 47 and 48 threaded thereon, along with the other bolts and nuts (not shown) releasably clamp the membrane means 40 between the O-ring 39 and the groove 38 in a manner effective to prevent liquid travel along the membrane means outwardly of the O-ring. The tubular projections 22 and 23 on chamber member 11 are connected into an external recirculating system indicated diagrammatically as comprising three-way valves 49 and 50, pump 51, vented reservoir 52, funnel 53, and drain 54.

The electrical circuitry of the instrument 10 illustrated in the drawings comprises a direct current source 55, preferably having an output voltage of from about 30 to about 250 volts. Switch means, for example in the form of a rotary electrical switch 56, provides for selective connection of the source 55 to the various electrodes in the chamber members 11 and 12.

The illustrated switch 56 has a rotor 57 of electrically insulating material fixedly mounted on a rotary shaft 58 and having a knob portion 59 for manual engagement. Alternatively, the shaft 58 may be drivingly connected to suitable operator means capable, for example, of rotating the shaft and rotor 57 to selected positions in timed sequence in accordance with a predetermined program.

Mounted on the periphery of the rotor 57 are a pair of electrically conductive arcuate shoes 60 and 61 which are respectively electrically connected to resilient electrical contact members 62 and 63 carried by and projecting from the periphery of rotor 57. Stationary resilient electrical contacts 64 and 65 are suitably mounted adjacent the periphery of rotor 57 for sliding electrical contact with the shoes 60 and 61, respectively, as shown. Mounted adjacent the periphery of the rotor 57, for selective electrical contact by the resilient rotor contact 62, are preferably equally spaced stationary contacts 66, 67, 68, and 69 as shown. Similarly mounted adjacent the periphery of the rotor 57 for selective electrical contact by the resilient rotor contact 63 are preferably equally spaced stationary contacts 71, 72, 73, and 74.

As shown in the electrical diagram of FIG. 1, the stationary resilient contact 64 is connected in circuit with the negative terminal of source 55, and the stationary resilient contact 65 is connected in circuit with the positive terminal of said source. The electrode 26 is connected in circuit with the stationary contacts 69 and 71, whereas the electrode 27 is connected in circuit with the stationary contact 72, and electrode 28 is connected in circuit with the stationary contact 73. Electrode 42 is connected in circuit with the stationary contacts 66 and 74, whereas electrode 43 is connected in circuit with the stationary contact 67 and electrode 44 is connected in circuit with the stationary contact 68.

Prior to the placement of the membrane means 40, between the walls 18 and 31 of the chamber members 11 and 12, respectively, target nucleic acid (RNA and DNA) is extracted from a sample containing the same and is denatured, i.e. converted to single-stranded form, in accordance with the procedure of Maniatis et al. The extracted single-stranded target nucleic acid sequences are then bound to a nitrocellulose filter in an irreversible manner by applying the same to the selected filter, and then baking it at a temperature of 70° C. for about 1 to about 2 hours under reduced pressure as aforedescribed. The filter, with the sample target nucleic acid sequences bound thereto is then prehybridized following the procedure of Grunstein et al by placement in a prehybridizing buffer which blocks nonspecific binding sites on its surface. The filter 41 is then placed in laminate relation with a sheet of pre-wet dialysis membrane, for example, Spectra/Por ®3787-D10, with the side of the filter having the target nucleic sequences bound thereto facing the dialysis membrane. The thus produced laminate membrane means 40 is then clamped by the bolts 46 and nuts 48 in the position shown in FIG. 1, after any air bubbles between the dialysis membrane and the filter have been forced out. The laminate is so arranged that filter 41 is disposed on the side of the dialysis membrane facing the chamber member 12 as shown. The membrane means 40 extends tightly across the apertures 20 and 35, and the filter 41 is in continuous face to face contact with the dialysis membrane.

With the chamber members 11 and 12 and membrane means 40 in the assembled relationship as shown in FIG. 1, the switch rotor 57 is turned clockwise an amount sufficient to move the shoes 60 and 61 out of engagement with the contacts 64 and 65, so that no current flows from the source 55 to any of the electrodes. The three-way valve 49 is then rotated 90 degrees in a counterclockwise direction from the position thereof shown in FIG. 1, and an aqueous buffer solution for example Buffer C described hereinafter, is introduced through the funnel 53, valve 49 and bore 24 into the interior of the chamber member 11 to fill the latter. Any air bubbles adherent to the dialysis membrane of the membrane means 40 are removed by turning the chamber members 11 and 12 on their sides. The three way valve 49 is then turned to a position 90 degrees clockwise from the position thereof shown in FIG. 1, and a supply of the aqueous buffer is delivered to the reservoir 52, after which the valve 49 is returned to the position of FIG. 1.

Hybridization buffer for example Buffer B described hereinafter containing 200,000 CPM/ml of labeled single-stranded nucleic acid probe complementary to the target sequences bound to the filter 41 is then added to the chamber member 12 through the bore 37 of the tubular projection 36. Chamber member 12 is completely filled and is turned as necessary to remove from filter 41 any bubbles trapped against the surface thereof. The hybridization step is initiated by starting the pump 51 and moving the switch rotor 57 to the position thereof shown in FIG. 1 wherein the numeral 1 on the rotor is in registry with the index mark.

Operation of the pump 51 causes circulation of the buffer solution from the reservoir 52 through the chamber member 11 and back to the reservoir 52 at which any bubbles are vented from the solution. The recirculating buffer flowing through the chamber member 11 wipes the side of the dialysis membrane facing the chamber member 11 and carries with it any bubbles on the surface thereof formed in chamber member 11. Such bubbles are then vented from the receptacle 52. The recirculating system also provides a cooling function for the buffer solution, thereby maintaining said solution at a safe temperature level which avoids effervescence. Fewer bubbles are generated within the chamber member 12, and they are vented through the bore 37 of the tubular projection 36. Cooling of the hybridization solution in the chamber member 12 is not required, since over heating has not been found to be a problem.

Placement of the switch rotor 57 in the position of FIG. 1 connects the electrode 42 in chamber member 12 with the negative terminal of source 55, and the electrode 26 in chamber member 11 with the positive terminal thereof. A voltage, preferably of from 80 to about 100 volts, is thus applied across the electrodes 42 and 26, causing a direct current of about 115 milliamperes to flow from electrode 42 (cathode) to the electrode 26 (anode) through the hybridization medium in chamber member 12 and the buffer solution in chamber member 11. The negatively charged probe molecules in chamber member 12 are caused to electrophoretically migrate toward the positively charged electrode 26 in chamber member 11. The probe molecules can pass through the filter 41, but cannot pass through the dialysis membrane. As a result, after from about 2 to about 7 minutes of such electophoresis, most of the probe molecules in the chamber member 12 are packed against the dialysis membrane in intimate contact with the sample target sequences bound to the side of the filter 41 facing the dialysis membrane. Such concentration of the probe molecules causes a dramatic increase in the incidence of collisions of the probe molecules with the bound target sequence molecules and is effective to cause annealing of the probe molecules to the target sequences at a dramatically accelerated rate.

After the probe molecules are thus concentrated between the filter 41 and the dialysis membrane in intimate contact with the target sequences bound to the filter 41, the unannealed probe molecules are caused to move laterally along the juxtaposed surfaces of the dialysis membrane and filter 41 to cause further acceleration of the incidence of collision of the probe molecules with the bound target molecules and annealing of the probe molecules with the target sequences at an even more accelerated rate. Such probe movement is effected by moving the rotor 57 successively at about 15 second intervals between the position thereof shown in FIG. 3, in which the numeral 2 is in registration with the index mark, and the position thereof shown in FIG. 4, wherein the numeral 3 is in registration with the index mark. Such alternate positioning of the rotor 57 is continued for from about 2 to about 30 minutes.

Figure 3:
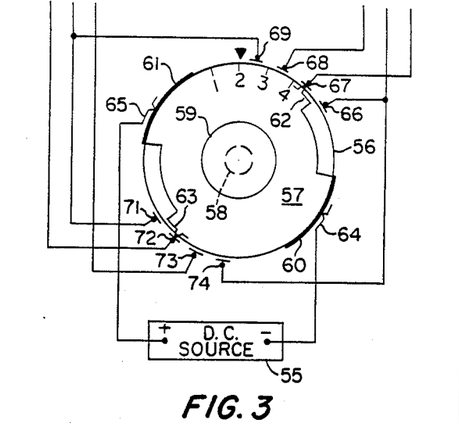
FIGS. 3, 4, and 5 illustrate various positions to which the rotary switch can be moved in the practice of the improved method.

Positioning of the rotor 57 in the position shown in FIG. 3 disconnects the electrodes 26 and 42 from the source 55 and connects the electrodes 27 and 43 to the positive and negative terminals of said source, respectively. This causes the unannealed probe molecules concentrated between filter 41 and the dialysis membrane to move along the interface between said membrane and filter toward the upper end of said interface within aperatures 20 and 35. Such probe movement results because the shortest current path beteen the electrode 43 and electrode 27 passes through the upper portions of said interface within the apertures 20 and 35. The unannealed probe molecules are therefore subjected to a force having a component directed upwardly along the membrane means 40, as well as a component directed toward said membrane means and tending to hold said probe molecules in contact with the latter.

Figure 4:
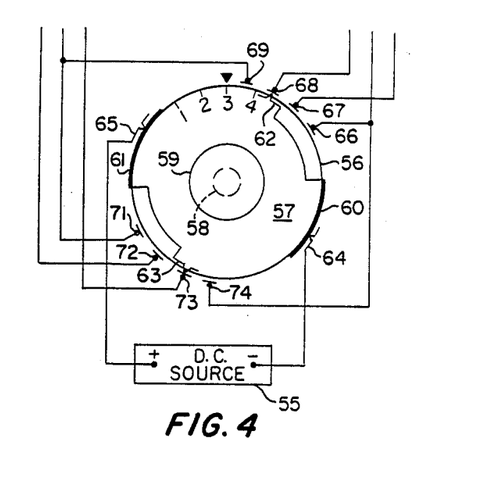

On the other hand, when the switch rotor 57 is in the position of FIG. 4, the electrodes 27 and 43 are disconnected from the source 55 and the electrodes 28 and 44 are connected to the positive and negative terminals of said source, respectively. As a result, the shortest current flow path from the electrode 44 to the electrode 28 passes through the lower portion of the interface between the dialysis membrane and filter 41 within the apertures 20 and 35. The unannealed probe molecules are therefore subjected to a force having a component directed downwardly along membrane means 40, as well as a component directed toward said membrane means and tending to hold said probe molecules in contact with the latter. This causes unannealed probe molecules which moved upwardly between the dialysis membrane and filter 41 when the rotor was in the position of FIG. 3, to move downwardly along the interface therebetween.

As the rotor 57 is sequentially positioned in the positions of FIGS. 3 and 4, the unannealed probe molecules are caused to move sequentially up and down along the interface between the dialysis membrane and filter 41.

Such probe movement can be analogized to a scrubbing action of the unannealed probe molecules along the target sequences bound to the filter 41, thereby providing for continuous active collisions between said probe molecules and bound target sequences.

It is understood, of course, that if desired, movement of the unannealed probe molecules along the aforementioned interface in directions other than up and down can be readily produced by appropriate electrode orientation. For example, in order to impart horizontal movement of the unannealed probe molecules along the surface of said membrane means 40, additional sets of electrodes such as electrodes 75 and 76 shown in dot and dash lines in FIG. 2 and corresponding to electrodes 27 and 43 and 28 and 44 can be oriented vertically. One set of such electrodes would be positioned in chamber member 11 closely adjacent the vertical sidewalls 15 and 16, as shown in FIG. 2, and the other set would be positioned in chamber member 12 closely adjacent vertical sidewall 33 and its opposite counterpart. The set of additional electrodes in chamber member 11 would be positioned adjacent the apertured vertical inner wall 18, and the other set in chamber member 12 would be positioned adjacent the apertured vertical inner wall 31.

After the electrophoretically enhanced annealing of the probe molecules with the bound target sequences produced by the aforedescribed alternate positioning of the switch rotor 57 has been completed, the filter 41 is subjected to a washing step which, in one version of the method of the invention, involves removal of said filter from its position shown in FIG. 1 by disassembly of the chamber members 11 and 12 following draining of the chamber members 11 and 12 and removal of the nuts 47 and 48 from the bolts 45 and 46, respectively. The filter is then washed under appropriate conditions to remove unannealed probe molecules adsorbed thereto in the electrophoretic hybridization step. Appropriate detection procedures are then carried out to determine the amount and location of labeled probe bound to the target sequences on the filter 41. Such procedures can be, for example, autoradiographic or colorimetric, depending upon the nature of the label attached to the bound probe.

Figure 5:
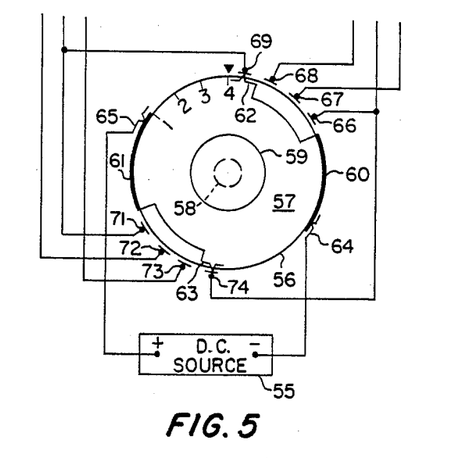

An alternative to the abovedescribed wash step is the rapid electrophoretic removal of unannealed probe molecules adsorbed to the filter 41. This step is carried out prior to the disassembly of the chamber members 11 and 12 aforementioned, and it is accomplished by moving the switch rotor 57 to the position of FIG. 5 in which the rotor numeral 4 is in registry with the index mark. In this position of the rotor the electrodes 27, 28, 43 and 44 are disconnected from the source 55, and the electrodes 26 and 42 are connected to the negative and positive terminals of the source 55, respectively. This reversal of polarity of the electrodes 26 and 42 causes unannealed probe molecules adsorbed to the filter 41, and any others that may be free in the hybridization solution, to migrate toward the electode 42 and away from the filter means 40. This reverse voltage is impressed on the electrodes 26 and 42 for from about 2 to about 15 minutes, after which the rotor 57 is rotated either clockwise or counterclockwise to a position in which the fixed resilient contacts 64 and 65 are again out of contact with the shoes 60 and 61, respectively.

With the current flow from electrode 26 to electrode 42 thus stopped, the hybridization solution in the chamber member 12 is then removed and replaced with a buffer solution, such as 0.030M sodium chloride, and 0.0030M sodium citrate, pH 7.5 in water. The rotor 57 is then returned to the position of FIG. 5 for from about 5 to about 10 minutes to remove any unannealed probe molecules remaining adsorbed to the filter 41. The buffer solutions are then removed from the chamber members 11 and 12, and said chamber members are disassembled as aforedescribed to permit removal of the filter 41 therefrom. The filter 41 is then dried and subjected to autoradiography or colorimetric detection, as appropriate, to determine the amount and location of labeled probe annealed to the target nucleic acid sequences bound to the filter 41.

An alternative to the laminate form of membrane means 40 used in the instrument of FIG. 1 is membrane means in which the target nucleic acid sequences are bound directly to the side of the dialysis membrane facing the chamber member 12. This arrangement obviates the need for the nitrocellulose or nylon filter 41 as a carrier for the target sequences, and retains the advantage of supporting the target sequences in the precise location at which the unannealed probe molecules are electrophoretically concentrated in the instrument. As with the laminate form of membrane means 40, the use of this alternative form of membrane means in the instrument of FIG. 1 is effective to substantially increase the incidence of collisions between unannealed probe molecules and the bound target molecules, thereby substantially enhancing the hybridization rate in both filter binding and sandwich filter binding formats.

The nucleic acid target sequence molecules prepared as described herein, can be bound to a cellulose dialysis type membrane following the procedure disclosed by Brüneman, H. et al in Methods Enz., Vol. 100 (1983), Academic Press, Inc. or Polsky-Cinkin, R. et al in Clin. Chem. (31(9), 1438–1443 (1985).

In order to illustrate the acceleration of the hybridization rate of a filter binding nucleic acid probe reaction through the method and means of the present invention, three different determinations were carried out. These three determinations provided the following indications, 1. The rate of hybridization under passive conditions at 42° C.;
2. The rate of hybridization produced by the practice of the method of the invention and use of the instrument illustrated in FIG. 1; and
3. The rate of hybridization in the instrument of FIG. 1 without any voltage applied to the electrodes thereof.

In preparation for such determinations, single-stranded $^{32}$P-labeled RNA probe was generated from a double-stranded DNA template according to the following protocol. Double-stranded DNA template derived from a plasmid was transcribed into single-stranded RNA using SP6 polymerase. The plasmid contained the SP6 phage promoter sequences; a portion of transmissible gastroenteritis virus (TGEV) cDNA; and a unique restriction endonuclease site following the cDNA sequence, in that order. The double-stranded plasmid was first cleaved at its unique restriction endonuclease site using the appropriate restriction enzyme.

The polymerase reaction contained 1.0 microgram of double-stranded plasmid; 50 mM Tris HCl, pH 7.5; 100 mM NaCl; 10 mM of MgCl$_2$; 10 mM dithiothreotol; 200 units of placental ribonuclease inhibitor; 0.5 mM concentrations of ATP, CTP, and UTP; 0.012 mM GTP; 10 microcuries of $^{32}$P-GTP; and 10 units of SP6 polymerase. The polymerase reaction was allowed to incubate for 60 minutes at 40° C., after which one unit of DNAase enzyme (RNAase free) was added and the reaction was incubated for 30 minutes at 37° C. The reaction was terminated by phenol/chloroform extraction, followed by chloroform extraction, and was then precipitated three times with ammonium acetate and ethanol to remove unreacted $^{32}$P-labeled nucleotides. The purified probe was then resuspended in water.

Nitrocellulose filters having target DNA sequences bound to one surface thereof were prepared as follows. Total cellular RNA was prepared from a mixture of Madin-Darby bovine kidney (MDBK) cells obtained from MA Bioproducts, Inc., Building 100, Biggs Ford Road, Walkerville, MD 21793, and monolayers of swine testicle cells obtained from the National Animal Disease Center, P.O. Box 70, Ames, Iowa 50010. The latter cells were infected at a multiplicity of greater than 10:1 with swine transmissible gastroenteritis virus (TGEV-ST) obtained from American Type Culture Collection, 12301 Park Lawn Drive, Rockville, MD 20852. A first portion of the total cellular RNAs (MDBK RNA) was mixed with water in a first eppendorf tube at a concentration of 4 micrograms per microliter. The remainder of the MDBK RNA was mixed with water in a second eppendorf tube at a concentration of 5 micrograms per milliliter, along with 0.5 micrograms TGEV-ST RNA per milliliter.

The eppendorf tubes containing the RNA were then boiled in a water bath for 4 minutes, and the contents thereof were then diluted 4:1 with a solution of 3.0M NaCl, and 0.3M sodium citrate pH 7.0 in water. Two microliter portions of each of the solutions in the eppendorf tubes were applied to one side of a fresh nitrocellulose sheet (Schleicher and Schuell, Catalog No. BA85) inside a pair of spaced apart smaller marker-drawn circles, respectively, each of which was within a larger circle having a diameter about equal to those of apertures 20 and 35, for example, ⅜ inch. The respective smaller circles werre marked to identify the particular RNA solution applied therewithin. The amount of MDBK RNA alone applied within one of the smaller circles of each pair was 1.0 microgram, and the amount of RNA applied to the other smaller circle of each pair was 1.0 microgram MDBK RNA plus 100 nanograms TGEV-ST RNA. The aforementioned RNA solutions were respectively applied to the smaller circles within about 15 of the larger circles drawn on the nitrocellulose sheet.

The nitrocellulose sheet with the RNA solutions applied to one side thereof was baked at 70° C. under a vacuum of less than 1 psi for 1½ hours to covalently fix the RNAs to the nitrocellulose sheet. The nitrocellulose sheet was then cut into squares of, for example, one square inch, each square containing one of the larger marker-drawn circles disposed centrally therein. The squares of nitrocellulose sheet were then prehybridized against buffer A in a sealed bag overnight at 42° C. and were retained in the bag until later used as described hereinafter. Buffer A was comprised of 50% formamide (v/v); 0.8M NaCl; 0.05M sodium phosphate, pH 6.5; 0.001M EDTA; 0.05% ficoll; 0.05% polyvinylpyrrolidone; 0.05% bovine serum albumin; 0.25% single-stranded (pre-boiled) salmon sperm DNA; 0.05% sodium dodecylsulfate; and 50% water (v/v).

Run No. 1—Passive hybridization

The rafte at which single-stranded RNA probe finds its nitrocellulose-bound complementary RNA target was determined by placing in a plastic tray containing 20 ml of Buffer A, four of the prehybridized filter squares prepared as afordescribed. The buffer A in the tray contained 200,000 CPM/ml of the purified single-stranded $^{32}$P-probe described above (hereinafter referred to as probe). The plastic tray was placed in a water bath at 42° C., and a different one of the four filter squares plus TGEV-ST RNA was removed from the probe solution at each of the times of 30 minutes, 1 hour, 2 hours, and 3 hours, after the start of incubation.

Immediately after removal from the above hybridization solution the filter squares were washed at 65° C. for 90 minutes in a buffer composed of 300 ml of a water solution of 0.03M NaCl; 0.003M sodium citrate, pH 7.0; and 0.2% sodium dodecylsulfate. The removed filter squares were then air dryed and mounted on a sheet of Whattman 3MM paper.

Run No. 2—Hybridization under electrophoretic pressure

For the following test runs 2 to 5 Buffers B and C were prepared. 250 ml of Buffer B were prepared which contained 0.02M NaPO$_4$, pH 6.5; 0.2M NaCl; 0.001M EDTA; 0.05% bovine serum albumin; and 0.05% sodium dodecylsulfate in water. One liter of Buffer C was prepared which contained 0.05M Tris.HCl, pH 7.5; 0.01M sodium acetate; and 0.001M EDTA in water. In each of test runs, the instrument of FIG. 1 was used. A fresh prewet dialysis membrane (Spectra/Por ®3787-D10) was used in each run. In each of Runs 2, 3, 4 and 5 a fresh square of prehybridized nitrocellulose filter prepared as aforedescribed was used.

In assembling the membrane means, the dialysis membrane was wet with Buffer C when the nitrocellulose filter square was placed thereon, the presence of the buffer excluding any air bubbles between the membrane and the filter on assembly. For each of the runs the side of the nitrocellulose filter square to which the RNA was applied was placed in face-to-face surface contact with the dialysis membrane as the latter was stretched over the O-ring 39, thereby producing the laminate membrane means which was thereupon clamped between the chamber members 11 and 12 by the use of the bolts 45 and 46 and cooperating nuts 47 and 48. Such clamping squeezes the dialysis membrane and the filter 41 tightly together.

With the chamber members 11 and 12 in the assembled relation of FIG. 1, Buffer B containing 200,000 CPM/ml of the above-described $^{32}$P-single-stranded RNA probe was placed into the chamber member 12, and the chamber member 11 was filled with Buffer C. A supply of Buffer C was also supplied to the reservoir 52 in the manner described earlier herein. The two chambers were filled with their respective solutions without any gas bubbles in contact with either the membrane means or the platinum electrodes. The pump 51 was started to initiate circulation of Buffer C through the chamber member 11 and venting at the reservoir 52 of any bubbles generated in said buffer. The aforedescribed assembly procedure was followed for each of the runs, and each run was begun with new hybridization Buffer B containing 200,000 CPM/ml of $^{32}$P-probe, new Buffer C, a fresh one of the RNA-containing nitrocellulose filter squares, and a new pre-wet dialysis membrane.

Run No. 2 was for the purpose of determining the rate of nucleic acid hybridization produced by the method and means of the present invention. In this run a prehybridized filter square 41 prepared as aforedescribed was used, and the run was begun by turning the switch rotor 57 to the position of FIG. 1, in which it was allowed to remain for five minutes. During this time interval direct current (115 mAmps at 80 volts) flowed through Buffers B and C from the negatively charged electrode 42 in chamber member 12 to the positively charged electrode 26 in chamber member 11. The switch rotor 57 was then moved to the position of FIG. 3 in which it was allowed to remain for 15 seconds, after which it was moved to the position of FIG. 4, where it was allowed to remain for 15 seconds. The switch rotor 57 was thereafter alternated between the positions of FIGS. 3 and 4 at 15 second intervals for 10 minutes, to thereby provide a total hybridization time of 15 minutes, after which the rotor was turned to a position in which the resilient contacts 64 and 65 were out of engagement with the shoes 60 and 61, respectively to terminate current flow from the source 55.

The instrument chamber members 11 and 12 were then emptied and disassembled, and the nitrocellulose filter square with the probe/target sequence complexes bound thereto was removed and washed in a solution of 0.03M NaCl; 0.003M sodium citrate, pH 7.0; and 0.2% sodium dodecylsulfate in 300 ml of water at 65° C. for 90 minutes. The filter square was then air dried and mounted on the same sheet of Whattman 3MM paper as that on which the filter squares from Run 1 were mounted.

Run No. 3—Hybridization under electrophoretic pressure

This run was identical with Run No. 2, except that the alternations in the position of the rotor 57 between the positions of FIGS. 3 and 4 took place for 5 minutes, rather than 10 minutes, so that the total hybridization time was 10 minutes.

Run No. 4—Hybridization without electrophoretic pressure

This run was identical to Run No. 2 except that the switch rotor 57 was placed in a position in which resilient contacts 64 and 65 were out of engagement with the shoes 60 and 61, respectively, so that no voltage was applied to any of the electrodes. This run was made for the purpose of determining the difference in hybridization rate under the same conditions as Run 2 but without electrophoretic pressure.

Run No. 5—Hybridization without electrophoretic pressure

This run was identical with Run No. 4, except that the hybridization was allowed to proceed for 10 minutes, rather than 15 minutes.

All of the filter squares from Runs 1 through 5, being mounted on the same sheet of Whattman 3MM paper, were then autoradiographed for 72 hours in a light-tight cassette using x-ray film. The developed x-ray film from the above autoradiography showed distinct dark spots in the exact shape and location of the smaller circles on the filter squares within which target RNAs were bound. The density of each spot and of the background of the developed x-ray film was determined in a quantitive manner using a visible light scanner set at 570 nanometers wavelength. The results from the scanner were normalized by subtracting the background of the x-ray film itself, and appear in Table 1.

TABLE 1

| Run No. | | Density Units |
|---|---|---|
| Passive Hybridization In Tray | | |
| 1. | (a) MDBK RNA alone, 3 hrs. | 9 |
| | (b) 100 ng TGEV-ST RNA + MDBK RNA, 3 hrs. | 155 |
| | (c) 100 ng TGEV-ST RNA + MDBK RNA, 2 hrs. | 86 |
| | (d) 100 ng TGEV-ST RNA + MDBK RNA, 1 hr. | 46 |
| | (e) 100 ng TGEV-ST RNA + MDBK RNA, 30 min. | 9 |
| Electrophoretic Pressure Hybridization In Instrument of FIG. 1, Voltage Applied | | |
| 2. | (a) MDBK RNA alone, 15 min. | 7 |
| | (b) 100 ng TGEV-ST RNA + MDBK RNA, 15 min. | 50 |
| 3. | 100 ng TGEV-ST RNA + MDBK RNA, 10 min. | 27 |
| Passive Hybridization In Instrument of FIG. 1, No Voltage Applied | | |
| 4. | (a) MDBK RNA alone, 15 min. | 6 |
| | (b) 100 ng TGEV-ST RNA + MDBK RNA, 15 min. | 10 |
| 5. | 100 ng TGEV-ST RNA + MDBK RNA, 10 min. | 7 |
| | X-ray film background | 0 |

The data in Table 1 demonstrates that hybridization for 15 minutes by the method and means of the invention as set forth in Run No. 2(b), produces a somewhat greater signal than one hour of passive hybridization as set forth in Run 1(d). Table 1 also demonstrates that hybridization in Buffer B without voltage applied as in Runs 4(a), 4(b) and 5, produces essentially a background level of signal, whereas hybridization in Buffer B with voltage applied, whether for 10 minutes as in Run 3, or 15 minutes as in Run 2(b), produces a very significant signal. It is apparent, therefore, that electrophoretic pressure, as used in the method and means of the present invention, has a substantial rate enhancing effect on the hybridization of the RNA probe with its complementary target bound to the filter. More particularly, it will be observed by comparing the results of Run 2(b) with the results of Run 4(b), that the rate of electrophoretic pressure hybridization is approximately 5 times faster than passive hybridization under the same conditions, but without the electrophoretic pressure.

The method and means of the invention have a number of advantages over the prior art used for nucleic acid probe hybridization. A particularly important aspect of the invention is that nucleic acid probe/target sequence hybridization and removal from the filter of unannealed probe molecules adsorbed thereto can be accomplished in drammatically less time than was heretofore possible, for example, in the range of from 15 to 30 minutes. Moreover, the hybridization and wash steps of a nucleic acid probe assay can be carried out without removal of the filter from the instrument in which the hybridization takes place.

The method and means of the invention readily lend themselves to automation and are equally applicable to the use therein of isotopic, as well as nonisotopic labelled nucleic acid probes in either the filter binding or sandwich filter binding format. Moreover, the speed and direction of movement of the concentrated unannealed probe molecules along the surface of the membrane means to which the target sequences are bound can be electrically controlled by adjustment of the orientation and configuration of the electrode means, as well as by adjustment of the voltage impressed thereon.

Another advantage of the invention is that the means for practicing the method can be simplified by forming the membrane means of a dialysis membrane to which the target sequences are bound, thereby eliminating the need for binding the target sequences to a nitrocellulose or nylon filter, while retaining the ability to practice hybridization in either the filter binding or sandwich filter binding formats.

It is understood that various other changes and modifications in the illustrated embodiment of the invention will suggest themselves to those skilled in the art, and that all of such changes are contemplated as may come within the scope of the appended claims.

What is claimed is:

1. The method comprising the steps of binding first nucleic acid molecules to membrane means comprising at least a liquid permeable membrane impermeable to nucleic acid molecules; contacting said membrane means and first molecules with an aqueous medium containing second nucleic acid molecules; and then passing a first electric current through said aqueous medium and said membrane means in a direction to move the second nucleic acid molecules electrophoretically toward said membrane means and into contact with said bound first nucleic acid molecules.

2. The method of claim 1 wherein said first and second nucleic acid molecules are single-stranded.

3. The method of claim 1 which comprises the further step of passing a second electric current through said medium in a direction electrophoretically to move in a second direction generally parallel to said membrane means second nucleic acid molecules concentrated at said membrane means by said first electric current, to thereby cause enhanced contact of said first and second molecules.

4. The method of claim 3 which comprises the further step of passing a third electric current through said medium in a direction electrophoretically to move second molecules concentrated at said membrane means in a predetermined third direction generally parallel to said membrane means.

5. The method of claim 4 wherein said second and third directions of movement of said second nucleic acid molecules are substantially opposite, and said second and third electric currents are passed through said medium successively to thereby move second molecules concentrated at said membrane means successively in opposite directions generally parallel to said membrane means.

6. The method of claim 5 wherein said movement of second molecules responsive to said second and third electric currents is produced by electrophoretic forces having components directed parallel to said membrane means, as well as components directed toward said membrane means.

7. The method of claim 3 wherein said movement of second molecules responsive to said second electric current is produced by electrophoretic forces having components directed parallel to said membrane means, as well as components directed toward said membrane means.

8. The method of claim 1 wherein said first electric current is passed through said medium for from about 2 to about 7 minutes.

9. The method of claim 4 wherein said second and third electric currents are respectively passed through said medium for from about 1 to 15 seconds.

10. The method of claim 9 wherein said first electric current is passed through said medium for from about 2 to about 7 minutes, and second and third electric currents are thereafter successively passed through said medium for from about 1 to about 30 minutes each.

11. The method of claim 1 wherein said first nucleic acid molecules are target molecules and the binding thereof to said membrane means is direct, and said second nucleic acid molecules are labeled probe molecules.

12. The method of claim 1 wherein said first nucleic acid molecules are target molecules and the binding thereof to said membrane means is through unlabeled probe molecules complementary thereto, and said second nucleic acid molecules are labeled probe molecules.

13. The method of claim 1 which comprises the further step of thereafter passing an electric current through said medium in a direction opposite to that of said first electric current, thereby electrophoretically to move away from said membrane means second nucleic acid molecules concentrated thereat.

14. The method of claim 1 wherein said second nucleic acid molecules are complementary to said first nucleic acid molecules and are labeled, said second nucleic acid molecules tending to become bound to said bound first nucleic acid molecules upon contact therewith, said method comprising the further steps of removing from said membrane means labeled molecules concentrated thereat which are not bound to said first nucleic acid molecules; and then quantifying any labeled molecules bound to said membrane means through said bound first nucleic acid molecules.

15. The method of claim 1 wherein said second nucleic acid molecules are complementary to said bound first nucleic acid molecules.

16. The method of claim 1 wherein said first molecules are target nucleic acid sequences; said second molecules are probe nucleic acid sequences complementary to said target sequences; said medium is a hybridization medium; and annealing of said first and second molecules at an accelerated rate is produced by impingement of said second molecules on the bound first molecules.

17. In combination, a receptacle having partition means separating first and second chambers therein, said partition means comprising membrane means including at least a liquid permeable membrane impervious to nucleic acid molecules; electrode means in each of said chambers adapted for connection to a direct current source; first nucleic acid molecules bound to said membrane means in said first chamber; a liquid hybridization medium in said first chamber in contact with the electrode means therein, with said membrane means, and with said first molecules; second nucleic acid molecules in said medium complementary to said first nucleic acid molecules; and an aqueous second liquid in said second chamber in contact with the electrode means therein and with said membrane means.

18. The combination of claim 17 wherein said first nucleic acid molecules are bound directly to said liquid permeable membrane.

19. The combination of claim 17 in which said membrane means further comprises a second membrane in laminate relation with said liquid permeable membrane and to which said first nucleic acid molecules are bound, said second membrane being permeable to liquid and to said second nucleic acid molecules.

20. The combination of claim 19 wherein said first nucleic acid molecules are bound to the surface of said second membrane facing said liquid impermeable membrane.

21. The combination of claim 17 wherein said partition means comprises liquid impermeable wall means formed with orifice means, said membrane means extending across and closing said orifice means.

22. The combination of claim 21 wherein the electrode means in said first and second chambers comprise first and second electrodes disposed in said chambers, respectively, said electrodes being adjacent an axis which extends generally normal to said membrane means and generally centrally through said orifice means.

23. The combination of claim 22 wherein there is switch means in circuit with said first and second electrodes and with a source of direct current for selectively connecting said first electrode to the negative terminal of said source and said second electrode to the positive terminal of said source.

24. The combination of claim 23 wherein said switch means can alternatively connect said first electrode to the positive terminal of said source and said second electrode to the negative terminal of said source.

25. The combination of claim 22 wherein the electrode means in said first and second chambers comprise a first pair of third and fourth electrodes disposed in said chambers, respectively, each of said third and fourth electrodes being spaced laterally from said axis.

26. The combination of claim 21 wherein said orifice means comprises a cylindrical bore extending through said wall means.

27. The combination of claim 20 wherein the electrode means in said first and second chambers comprise a first pair of third and fourth electrodes disposed in said chambers, respectively, and spaced laterally in the same direction from said axis.

28. The combination of claim 27 wherein there is switch means in circuit with said third and fourth electrodes and with a source of direct current, for selectively connecting said third electrode to the negative terminal of said source and said fourth electrode to the positive terminal of said source.

29. The combination of claim 27 wherein said first and second electrodes are remote from said wall means, and said third and fourth electrodes are adjacent said wall means.

30. The combination of claim 29 wherein there is switch means in circuit with all of said electrodes and with a source of direct current for selectively connecting said first and second electrodes, respectively, to the negative and positive terminals of said source, and for altenatively connecting said third and fourth electrodes, respectively, to said negative and positive terminals.

31. The combination of claim 27 wherein the electrode means in said first and second chambers additionally comprise a second pair of said third and fourth electrodes disposed in said chambers, respectively, said second pair of third and fourth electrodes being spaced on the opposite side of said axis from said first pair of third and fourth electrodes.

32. The combination of claim 31 wherein said first and second electrodes are each disposed remote from said wall means, and said third and fourth electrodes of each pair thereof are each disposed adjacent said wall means.

33. The combination of claim 31 wherein there is switch means in circuit with said first and second pairs of third and fourth electrodes and with a source of direct current, for selectively connecting the third electrode of said first pair to the negative terminal of said source and the fourth electrode of said first pair to the positive terminal of said source, and for alternatively connecting the third electrode of said second pair to the negative terminal of said source and the fourth electrode of said second pair to the positive terminal of said source.

34. The combination of claim 17 wherein there is switch means in circuit with each of said electrode means and with a source of direct current for selectively connecting said electrode means to said source.

35. The combination of claim 34 wherein said switch means has a position in which the negative terminal of the source is connected to the electrode means in said first chamber and the positive terminal of said source is connected to the electrode means in said second chamber, said switch means also having a position wherein the positive terminal of said source is connected to the electrode means in said first chamber and the negative terminal of said source is connected to the electrode means in said second chamber.

36. The combination of claim 17 which additionally comprises means for circulating said aqueous second liquid externally of said second chamber.

37. The combination of claim 36 wherein said means for circulating said aqueous second liquid incorporates debubbling means.

38. In combination, a receptacle having partition means separating first and second chambers therein, said partition means comprising membrane means including at least a liquid permeable membrane impervious to nucleic acid molecules; electrode means in each of said chambers adapted for connection to a direct current source; first nucleic acid molecules bound to said membrane means in said first chamber; and aqueous first liquid medium in said first chamber in contact with the electrode means therein, with said membrane means, and with said first molecules; second nucleic acid molecules in said first liquid medium complementary to said first nucleic acid molecules; and an aqueous second liquid medium in said second chamber in contact with the electrode means therein and with said membrane means.

* * * * *

UNITED STATES PATENT AND TRADEMARK OFFICE
CERTIFICATE OF CORRECTION

PATENT NO. : 4,787,963
DATED : November 29, 1988
INVENTOR(S) : William P. Mac Connell Page 1 of 2

It is certified that error appears in the above-identified patent and that said Letters Patent is hereby corrected as shown below:

First Page, left hand column, line 24, under "PUBLICATIONS", "Meinkoth, J." should read --Meinkoth, J. et al.,--; line 28, "DNH" should read --DNA--; line 33, "Wetmur, V." should read --Wetmur, J.--; right hand column, line 2, "(1974)" should read --(1975)--; After line 5, add: --Bunemann, H. et al., "Hybrid Selection of Specific RNAs Using DNA Covalently Coupled to Macroporous Supports", Methods Enz., Academic Press, Inc., Vol. 100, pp. 400-407 (1983).-- --Polsky-Cynkin, R. et al., "Use of DNA Immobilized on Plastic and Agarose Supports to Detect DNA by Sandwich Hybridization", Clin. Chem., Vol. 31, No. 9, pp. 1438-1443 (1985).--. Column 1, line 25, "year" should read --years--. Column 7, line 15, cancel "the" and substitute --a second central--; Cancel line 16; line 17, cancel "a second central" and substitute --the--; line 22, cancel "a" and substitute --an upper--; line 22, before "disposed" insert --spaced laterally from the axis of the bores 20 and 35, is--. Column 8, line 47, cancel "and", second instance, and substitute --or--. Column 9, line 14, after "solution" insert --,--. Column 12, line 36, "(31(9)" should read --31(9)--. Column 13, line 39, "werre" should read --were--; line 66, "rafte" should read --rate--. Claim 27, line 28, cancel "20" and substitute --22--.

UNITED STATES PATENT AND TRADEMARK OFFICE
CERTIFICATE OF CORRECTION

PATENT NO. : 4,787,963

DATED : November 29, 1988

INVENTOR(S) : William P. Mac Connell

It is certified that error appears in the above-identified patent and that said Letters Patent is hereby corrected as shown below:

Claim 38, line 46, cancel "and" and substitute --an--.

Signed and Sealed this

Sixth Day of June, 1989

*Attest:*

DONALD J. QUIGG

*Attesting Officer*     *Commissioner of Patents and Trademarks*